United States Patent [19]

Ford

[11] 4,045,998

[45] Sept. 6, 1977

[54] TEMPERATURE CONTROL SYSTEM

[75] Inventor: Gregory A. Ford, Bartlesville, Okla.

[73] Assignee: Phillips Petroleum Company, Bartlesville, Okla.

[21] Appl. No.: 662,778

[22] Filed: Mar. 1, 1976

[51] Int. Cl.² ............................................ G01N 31/08
[52] U.S. Cl. ..................................... 73/23.1; 165/156
[58] Field of Search ................. 73/23.1; 165/154, 155, 165/156, 163, 60, 11; 23/232 C, 254 R

[56] References Cited

U.S. PATENT DOCUMENTS

| 1,554,654 | 9/1925 | Priser | 165/155 |
| 2,136,813 | 11/1938 | Dolison | 165/156 |
| 3,285,055 | 11/1966 | Reinecke | 73/23.1 |
| 3,290,482 | 12/1966 | Dodd et al. | 73/23.1 |
| 3,385,101 | 5/1968 | Roof | 73/23.1 |
| 3,477,501 | 11/1969 | Van Es | 165/154 |
| 3,585,842 | 1/1971 | Roof | 73/23.1 |
| 3,722,583 | 3/1973 | Fiedler | 165/156 |

Primary Examiner—Richard C. Queisser
Assistant Examiner—Stephen A. Kreitman

[57] ABSTRACT

A chromatographic analyzer for use in an explosive atmosphere is provided with a double-walled, dual passage helix heat exchanger. A heat exchange fluid, such as steam, is passed through one passage of the helix. A second fluid, such as air, is passed through the second passage and discharged into the insulated chamber of the chromatograph through the interspaces of the helix configuration.

5 Claims, 3 Drawing Figures

TEMPERATURE CONTROL SYSTEM

This invention relates to an apparatus for controlling the temperature of a system. In one aspect the invention relates to a chromatographic analysis system. In another aspect the invention relates to a chromatographic system adapted to operate in an explosive atmosphere.

In various industrial operations, there is a need for analytical procedures capable of continuously measuring the concentration of constituents in process streams. One analytical procedure which has become quite valuable for making such analysis involves chromatography. In elution chromatography, a sample of material to be analyzed is introduced into a column which contains a selective sorbent. A carrier gas is directed into the column so as to force the sample material therethrough. The sorbent attempts to hold the components of the mixture, whereas the carrier gas tends to force the components through the column. This results in the several components of the fluid mixture traveling through the column at different rates depending upon their affinity for the packing material. The column effluent thus consists initially of the carrier gas alone, the individual components of the fluid mixture appearing later at spaced intervals. The concentration of these components is determined by any suitable means, such as by thermal conductivity, infra-red and the like.

Analyses of this general type have proved to be quite useful in the analysis of process fluid mixtures. The process stream analyzer containing a chromatographic column or columns and the sample is maintained at a constant temperature, normally an elevated temperature, while the sample is being passed through the column or columns. To ensure maintenance of a constant temperature during analysis, the process stream analyzer is enclosed within a housing and the enclosed area and the equipment therein maintained at a constant temperature.

Resistance heating is generally employed in chromatographic analyzers to maintain a constant temperature. A fan is employed to circulate the air within the column housing thereby minimizing the temperature gradient throughout the housing.

It is often desirable to analyze process streams having one or more potentially explosive components. For such analyses or where the analyzers must be located in an explosive atmosphere, electrical resistance heating and electrical circulating fans are impractical. Resistance heating elements generally develop a high surface temperature, and fans suitable for use in an explosive atmosphere are generally bulky.

It is an object of this invention to provide an improved chromatographic apparatus.

It is another object of this invention to provide an improved heater for a chromatographic apparatus.

Other objects, advantages and features of the present invention will be readily apparent to those skilled in the art from the following description and drawing and the appended claims.

By the present invention there is provided an improved chromatographic analyzer having a novel heat exchange means comprising a double-walled, dual passage helix having a plurality of turns whereby a first fluid medium is passed through one passage in heat exchange relationship to a second fluid medium in the second passage, wherein one such fluid medium is discharged into the insulated housing of the chromatographic analyzer. The chromatographic analyzer of this invention is particularly suitable for the analysis of process streams in the direct control of processes.

Figure 1:
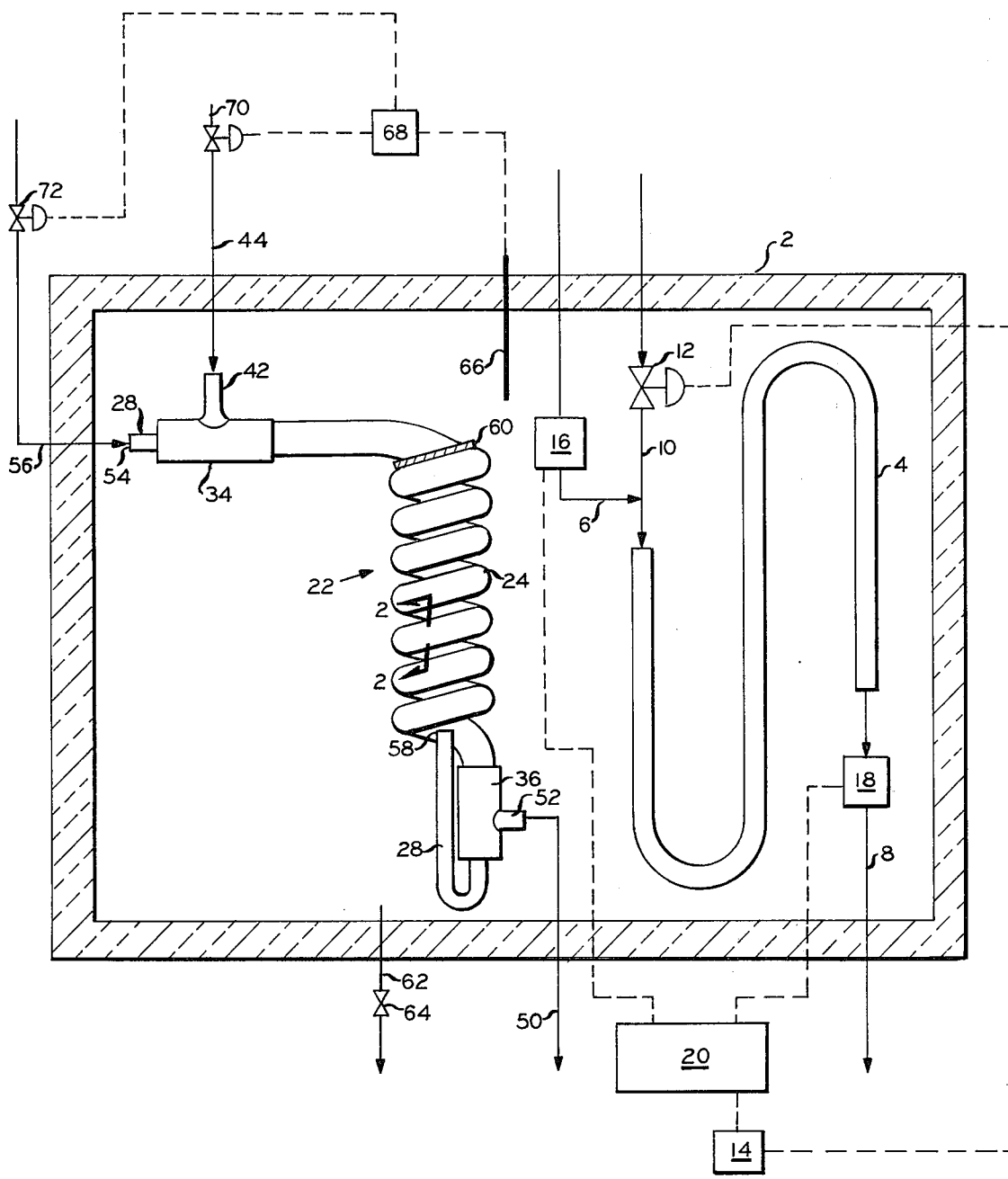
FIG. 1 is a schematic representation of a chromatographic analyzer in accordance with the present invention.

Referring now to the drawings and to FIG. 1 in particular, there is shown a housing 2 made of thermally insulating material. In housing 2 there is shown a conventional chromatographic column 4 which is filled with a packing material that selectively retards passage therethrough of constituents of a fluid mixture to be analyzed. A carrier gas is introduced into the first end of column 4 through a conduit 6. A conduit 8 removes the effluent from column 4. A sample conduit 10, having a control valve 12 therein, communicates with the first end of column 4. Valve 12 is opened periodically for a preselected time interval by means of a timer 14 so as to introduce a predetermined volume of fluid sample to be analyzed into column 4. Although shown schematically, valve 12 can be any type of sample valve known in the art which permits the introduction of a predetermined volume of fluid sample.

First and second sensing elements 16 and 18 are disposed in respective conduits 6 and 8. These elements are adapted to compare a property of the fluid flowing through the two conduits to provide an indication of the differences therebetween. These detecting elements are advantageously temperature sensitive resistance elements. The detecting elements are connected to a measuring circuit 20 which can be any suitable measuring circuit known in the art. Before the sample fluid is introduced into column 4, the carrier gas flows through conduits 6 and 8 so that elements 16 and 18 respond to the same fluid and have identical outputs. Valve 12 is then opened to introduce a sample into column 4. The carrier gas elutes the constituents of the sample from the column in sequence so that element 18 responds sequentially to these individual components.

Figure 2:
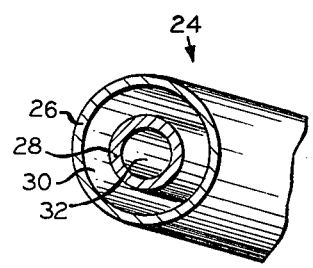
FIG. 2 is a partial cross-sectional view through the coil construction of FIG. 1 taken along the line 2—2.

The components within housing 2 are maintained at substantially the same temperature by heat exchange means 22 which comprises a helix having a plurality of spaced turns. The helix can be circular, as shown, or conical. Each turn of the helix is a convoluted section of double-walled, dual passage tubing 24. As shown in FIG. 2, tubing 24 consists essentially of an outer tubular member 26 and an inner tubular member 28 disposed within the outer tubular member 26. The space between the inner and outer members provides a first passage 30 for a first fluid medium, and the inner tubular member 28 provides a second passage 32 for a second fluid medium. Referring again to FIG. 1, the first end of the outer tubular member 26 is operably connected to supply fitting 34 and the second end to discharge fitting 36.

Figure 3:
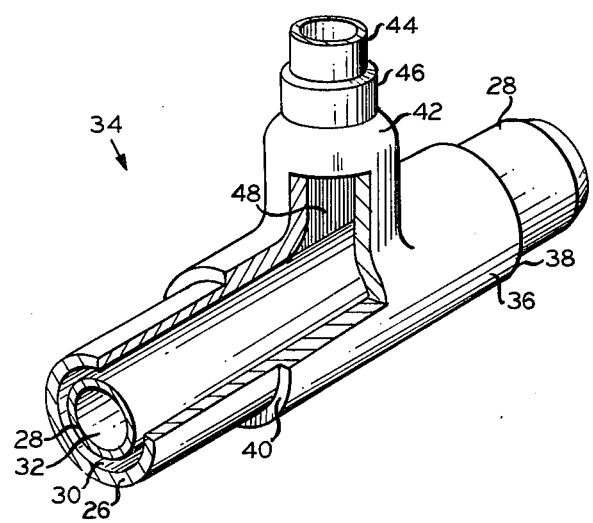
FIG. 3 is a perspective view, partially in cross section, illustrating a preferred form of fitting used at the inlet and outlet portions of the coil construction of FIG. 1.

The construction of fittings 34 and 36 and their manner of connection to the double-walled dual-passage tubing 24 is best understood with reference to FIG. 3. The fittings 34 and 36 are of generally T-shaped configuration. Since these fittings are substantially identical, only fitting 34 is shown. Fitting 34 has a cylindrical portion 36 defining opposite open ends 38 and 40. In the wall of cylindrical portion 36 there is provided a port 42 with an end section of a length of tubing 44 being connected to port 42 by a nut 46 or other coupling device known in the art.

The fitting 34 surrounds the first end portion of inner tubular member 28 with the end portion 40 being joined to the end of the outer tubular member 26. The opposite end portion 38 is of smaller diameter than end portion 40 and is sealed to the outer wall of inner tubular member 28 by soldering or other method known in the art. As such, fitting 34 provides a chamber 48 which is in direct communication with the first passage 30.

The first fluid medium is introduced into the port 42 of fitting 34 through conduit 44. A conduit 50 removes the first fluid medium from the first passage 30 through discharge port 52 in fitting 36.

The second fluid medium is introduced into the first end 54 of inner tubular member 28 through conduit 56. The second end 58 of inner tubular member 28 is adapted to discharge the second fluid medium into the interior of housing 2. In the embodiment shown, the second end 58 of the inner tubular member 28 is adapted to discharge the second fluid into one open end of the helix 22. In a more preferred embodiment, the opposite end of helix 22 is at least partially blocked by a plate member 60 which is secured to the opposite open end of the helix 22 by soldering or by other suitable means known in the art. In this preferred embodiment, the second fluid, after discharge from the second end 58 of the inner tubular member 28 flows into the inner space defined by the turns of the helix 22. The plate 60 blocks longitudinal flow of such fluid and forces the fluid to flow outwardly through the open spaces between the turns of the helix 22.

It is also within the scope of this invention to introduce the first fluid medium into the port 42 of fitting 34 and to discharge same into the interior of housing 2 through discharge port 52 of the fitting 36. In this embodiment the second fluid medium is introduced into the first end 54 of inner tubular member 28 through conduit 56. The second end 58 of inner tubular member 28 is adapted to discharge the second fluid medium into a discharge conduit, not shown.

Since the flow of the second fluid medium into the housing 2 produces a positive pressure with the housing, some means of relieving such pressure should be provided, such as by vent line 62, equipped with a one-way or relief valve 64.

A temperature sensing means 66, such as a thermocouple, transmits a signal to temperature controller 68 representative of the temperature inside housing 2. Temperature controller 68 manipulates valve 70 which regulates the flow of the first fluid medium through conduit 44 responsive to the output signal of temperature sensing means 66 and to a set-point signal applied to controller 68. Temperature controller 68 can also be adapted to manipulate valve 72 which regulates the flow of the second fluid medium through conduit 56.

The first and second fluid mediums can be any gas or liquid known in the art for heat exchange. Examples of suitable fluids include air, water, steam, nitrogen, glycol, glycerol, carbon dioxide and the like. In general, process chromatographic analyzers are operated at an elevated temperature. For such operation, the first fluid can be steam and the second fluid can be air. It may be desirable to operate such analyzer at a temperature below ambient temperature, in which case the first fluid can be a cooled fluid, such as water or glycol and the second fluid can be air.

The heat exchange means 22, in the embodiment shown in FIG. 1, acts as a forced convection heat exchanger. That is, heat exchange occurs between the first and second fluids during passage of the second fluid through the coils of the helix, and further heat exchange takes place as the second fluid is passed out between the spaced turns of the helix.

The heat exchange means can be so sized to fit an intended application. In this regard the relative sizes of the inner and outer tubular members and the inner diameter of the helix are not restricted to a particular range.

In accordance with a presently preferred embodiment, a heat exchange means of the type described hereinbefore was installed in a process chromatographic analyzer. Steam was passed through the first passage and air was passed through the second passage. The thermal gradient through the insulated chamber was found to be 4° F. In contrast, the same analyzer, using resistance heating had a thermal gradient through the chamber of 70° F.

Reasonable variations and modifications, which will be apparent to those skilled in the art, can be made in this invention without departing from the spirit and scope thereof.

I claim:
1. A chromatographic analyzer comprising:
an insulated housing;
a chromatographic column positioned within said housing, said column being filled with a packing material that selectively retards passage therethrough of constituents of the fluid mixture to be analyzed;
first conduit means passing through said housing and communicating between a source of carrier gas and the inlet of said column;
a first sensing element disposed within said housing and in said first conduit means to detect a property of the carrier gas flowing through said first conduit means;
second conduit means passing through said housing and communicating with said first conduit means downstream of said first sensing element for introducing a sample of the fluid mixture to be analyzed into said first conduit means;
third conduit means passing through said housing and communicating with the outlet of said column;
a second sensing element disposed within said housing and in said third conduit means to detect a property of the fluid flowing through said third conduit means;
means for comparing the outputs of said first and second sensing elements;
means disposed within said housing for maintaining the temperature of said housing at a substantially constant value comprising in combination, a helix having a plurality of spaced turns, said helix consisting essentially of an outer tubular member and an inner tubular member disposed within said outer tubular member, said inner tubular member having an outside diameter smaller than the inside diameter of said outer tubular member whereby the space between said inner and outer members provides a first passage for a first fluid medium and said inner tubular member provides a second passage for a second fluid medium; said outer tubular member having a first end and a second end, said inner tubular member having a first end, a first end portion, a second end and a second end portion; a first fitting disposed about and having one end sealed with respect to said first end portion of said inner tubular member and having the opposite end thereof operably connected to said first end of said outer tubular member and an inlet port in the wall of said first fitting; fourth conduit means passing through said housing and communicating between a source of supply of said first fluid medium and said inlet port of said first fitting; fifth conduit means passing through said housing and communicating between a source of supply of said second fluid medium and said first end of said inner tubular member; a second fitting disposed about and having one end sealed with respect to said second end portion of said inner tubular member and having the opposite end thereof operably connected to said second end of said outer tubular member and an outlet port in the wall of said second fitting; sixth condit means passing through said housing and communicating with said outlet of said second fitting; wherein said second end of said inner tubular member is adapted to discharge said second fluid into one open end of said helix;

means for determining the temperature within said housing and establishing a first signal responsive thereto; and means responsive to said first signal for controlling the flow from said source of said first fluid into said inlet port of said first fitting.

2. The analyzer of claim 1 wherein the opposite end of said helix is at least partially blocked by a plate member.

3. The analyzer of claim 2 wherein said helix is a circular helix.

4. A heat exchanger comprising:

a helix having a plurality of spaced turns, said helix consisting essentially of an outer tubular member and an inner tubular member disposed within said outer tubular member, said inner tubular member having an outside diameter smaller than the inside diameter of said outer tubular member whereby the space between and inner and outer members provides a first passage for a first fluid medium, said inner tubular member providing a second passage for a second fluid medium;

said outer tubular member having a first end and a second end;

said inner tubular member having a first end, a first end portion, a second end and a second end portion;

a first fitting disposed about and having one end sealed with respect to said first end portion of said inner tubular member and having the opposite end thereof operably connected to said first end of said outer tubular member and an inlet port in the wall of said first fitting;

means for connecting said inlet port with a source of supply of said first fluid medium;

means for connecting said first end of said inner tubular member with a source of supply of said second fluid medium;

a second fitting disposed about and having one end sealed with respect to said second end portion of said inner tubular member and having the opposite end thereof operably connected to said second end of said outer tubular member and an outlet port in the wall of said second fitting; and means for connecting said outlet port with means for disposing of said first fluid medium, wherein said second end of said inner tubular member is adapted to discharge said second fluid medium into one open end of said helix, and wherein the opposite end of said helix is at least partially blocked by a plate member.

5. The heat exchanger of claim 4 wherein said helix is a circular helix.

* * * * *